(12) United States Patent
Moskal et al.

(10) Patent No.: US 11,859,020 B2
(45) Date of Patent: Jan. 2, 2024

(54) INSULIN LIKE GROWTH FACTOR BINDING PROTEIN BIOACTIVE PEPTIDE FRAGMENTS

(71) Applicant: Northwestern University, Evanston, IL (US)

(72) Inventors: Joseph R. Moskal, Evanston, IL (US); Jeffrey S. Burgdorf, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/586,185

(22) Filed: Jan. 27, 2022

(65) Prior Publication Data
US 2022/0144896 A1    May 12, 2022

Related U.S. Application Data

(62) Division of application No. 16/924,745, filed on Jul. 9, 2020, now abandoned.

(60) Provisional application No. 62/873,418, filed on Jul. 12, 2019.

(51) Int. Cl.
| | | |
|---|---|---|
| *C07K 7/06* | (2006.01) | |
| *C07K 7/08* | (2006.01) | |
| *C07K 7/64* | (2006.01) | |
| *A61K 38/00* | (2006.01) | |
| *A61P 25/22* | (2006.01) | |
| *A61P 25/24* | (2006.01) | |
| *A61P 25/08* | (2006.01) | |
| *A61P 25/28* | (2006.01) | |
| *A61P 25/18* | (2006.01) | |
| *A61P 25/00* | (2006.01) | |
| *A61P 25/14* | (2006.01) | |

(52) U.S. Cl.
CPC ............... *C07K 7/64* (2013.01); *A61P 25/14* (2018.01); *A61P 25/22* (2018.01); *A61P 25/24* (2018.01); *C07K 7/08* (2013.01); *A61K 38/00* (2013.01)

(58) Field of Classification Search
CPC ... C07K 7/64; C07K 7/08; C07K 7/06; C07K 14/4743; A61P 25/22; A61P 25/24; A61P 25/08; A61P 25/18; A61P 25/28; A61P 25/00; A61K 38/00
See application file for complete search history.

(56) References Cited

U.S. PATENT DOCUMENTS

| | | | |
|---|---|---|---|
| 4,966,848 A | 10/1990 | Smith et al. | |
| 5,223,421 A | 6/1993 | Smith et al. | |
| 5,837,218 A | 11/1998 | Peers et al. | |
| 7,488,798 B2 | 2/2009 | Forbes | |
| 9,060,961 B2 | 6/2015 | Disis et al. | |
| 9,072,707 B2 * | 7/2015 | Hwang | A61K 38/10 |
| 2006/0153853 A1 | 7/2006 | Forbes | |
| 2008/0286287 A1 | 11/2008 | Russo et al. | |
| 2009/0075876 A1 | 3/2009 | Forbes | |
| 2014/0100160 A1 | 4/2014 | Hwang | |

FOREIGN PATENT DOCUMENTS

| | | |
|---|---|---|
| RU | 2640133 C1 * | 12/2017 |
| WO | WO-00/23469 A2 | 4/2000 |
| WO | WO-01/31019 A2 | 5/2001 |
| WO | WO-2006/034832 A2 | 4/2006 |
| WO | WO-2010/141811 A2 | 12/2010 |
| WO | WO-2014/165137 A1 | 10/2014 |

OTHER PUBLICATIONS

RU2640133, Google Patent English translation, pp. 1-10. 2017. (Year: 2017).*
A0A0A6YY89 from UniProt, pp. 1-3 integrated into UniProlKB/TrEMBL Feb. 4, 2015 (Year 2015).
Bachem—Peptide Trends May 2017, May 1, 2017, retrieved from https://www.bachem.com/service-support/newsletter/peptide-trends-may-2017, 7 pages.
Joo et al., "Cyclic Peptides as Therapeutic Agents and Biochemical Tools," Biomolecules & Therapeutics, 2012, 20(1):19-16.
Mark et al., "Diversity of Human Insulin-like Growth Factor (IGF) Binding Protein-2 Fragments in Plasma: Primary Structure, IGF-Binding Properties, and Disulfide Bonding Pattern," Biochemistry, 2005, 44: 3644-3652 (Year 2005).
Partial International Search Report and Invitation to Pay Additional Fees dated Oct. 14, 2020 in PCT/US2020/041327.

* cited by examiner

*Primary Examiner* — Julie Ha
(74) *Attorney, Agent, or Firm* — Foley & Lardner LLP

(57) ABSTRACT

Described herein are isolated peptides, compositions comprising the same, and methods of using such peptides or compositions in the treatment of depression, central nervous system disorders, and neurodevelopmental disorders.

5 Claims, 4 Drawing Sheets
Specification includes a Sequence Listing.

INSULIN LIKE GROWTH FACTOR BINDING PROTEIN BIOACTIVE PEPTIDE FRAGMENTS

CROSS-REFERENCE TO RELATED APPLICATIONS

This application is a Divisional of U.S. application Ser. No. 16/924,745, filed Jul. 9, 2020, which claims the benefit of U.S. Provisional Patent Application No. 62/873,418, filed Jul. 12, 2019, which is incorporated by reference herein in its entirety.

STATEMENT OF GOVERNMENT SUPPORT

This invention was made with government support under MH094835 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jan. 26, 2022, is named 121384-0169_SL.txt and is 813 bytes in size.

FIELD

The present invention relates generally to the field of treatment of neurodevelopmental disorders, central nervous system disorders, and depression. More specifically, the present invention involves treatment with insulin-like growth factor binding protein peptide fragments, variants thereof, and homologous peptides thereof.

SUMMARY

Provided herein, in one aspect, are isolated peptides having a length of 18 amino acids to 40 amino acids, comprising an amino acid sequence of KHGLYNLKQCKMSLNGQ (SEQ ID NO: 1). In some embodiments, the peptide comprises N-terminal carboxylation, C-terminal amidation, one or more halogens, or a combination thereof. In some embodiments, the peptide is cyclized.

Provided herein, in another aspect, is an isolated peptide consisting of an amino acid sequence of KHGLYNLKQCKMSLNGQ (SEQ ID NO: 1), or an isolated fragment of the peptide. In some embodiments, the fragment has a length of 4-16 amino acids. In some embodiments, the peptide comprises N-terminal carboxylation, C-terminal amidation, one or more halogens, or a combination thereof. In some embodiments, the peptide is cyclized.

Provided herein, in another aspect, are isolated peptides having a length of 18 amino acids to 40 amino acids, comprising an amino acid sequence having at least 85% sequence identity to SEQ ID NO: 1. In some embodiments, the peptide comprises an amino acid sequence having at least 90% sequence identity to SEQ ID NO: 1. In some embodiments, the peptide comprises an amino acid sequence having at least 95% sequence identity to SEQ ID NO: 1. In some embodiments, the peptide comprises N-terminal carboxylation, C-terminal amidation, one or more halogens, or a combination thereof. In some embodiments, the peptide is cyclized.

Provided herein, in another aspect, is an isolated fragment of a peptide, wherein the peptide consists of an amino acid sequence of SEQ ID NO:1, and the fragment has a length of 4-16 amino acids. In some embodiments, the fragment further comprises N-terminal carboxylation, C-terminal amidation, one or more halogens, or a combination thereof. In some embodiments, the fragment is cyclized.

Provided herein, in another aspect, are isolated peptides having a length of 7 amino acids to 20 amino acids and comprising an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, is an isolated peptide consisting of an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, is an isolated peptide having a length of 7 amino acids to 20 amino acids and comprising an amino acid sequence having at least 65% sequence identity to SEQ ID NO: 2. In some embodiments, the peptide comprises an amino acid sequence having at least 85% sequence identity to SEQ ID NO: 2. In some embodiments, the peptide comprises N-terminal carboxylation, C-terminal amidation, one or more halogens, or a combination thereof. In some embodiments, the peptide is cyclized.

Provided herein, in another aspect, is an isolated fragment of a peptide, wherein the peptide consists of an amino acid sequence of SEQ ID NO: 2, and the fragment has a length of 3-5 amino acids. In some embodiments, the peptide comprises N-terminal carboxylation, C-terminal amidation, one or more halogens, or a combination thereof. In some embodiments, the peptide is cyclized.

Provided herein, in another aspect, are pharmaceutical compositions comprising a peptide disclosed herein or a fragment disclosed herein and at least one pharmaceutically acceptable excipient.

Provided herein, in another aspect, are methods of treating depression in a subject in need thereof, comprising administering to the subject a therapeutically effective amount of a peptide disclosed herein or a fragment disclosed herein or a composition disclosed herein.

Provided herein, in another aspect, are methods of treating post-traumatic stress disorder (PTSD) in a subject in need thereof, comprising administering to the subject a therapeutically effective amount of a peptide disclosed herein or a fragment disclosed herein or a composition disclosed herein.

Provided herein, in another aspect, are methods of treating a central nervous system disorder in a subject in need thereof, comprising administering to the subject a therapeutically effective amount of a peptide disclosed herein or a fragment disclosed herein or a composition disclosed herein. In some embodiments, the central nervous system disorder is selected from autism spectrum disorders, bipolar disorder, catalepsy, depression, post-traumatic stress disorder (PTSD), encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Provided herein, in another aspect, are methods of treating a neurodevelopmental disorder in a subject in need thereof, comprising administering to the subject a therapeutically effective amount of a peptide disclosed herein or a fragment disclosed herein or a composition disclosed herein. In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof. In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome. In some embodiments, the motor disorders are developmental coordination disorder or stereotypic movement disorder.

Provided herein, in another aspect, are methods of treating Phelan-McDermid Syndrome in a subject in need thereof, comprising administering to the subject a therapeutically effective amount of a peptide disclosed herein or a fragment disclosed herein or a composition disclosed herein.

Provided herein, in another aspect, are methods of treating depression in a subject in need thereof, comprising administering to the subject a therapeutically effective amount of a peptide having a length of 7 amino acids to 20 amino acids and comprising an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, are methods of treating a central nervous system disorder in a subject in need thereof, comprising administering to the subject a therapeutically effective amount of a peptide having a length of 7 amino acids to 20 amino acids and comprising an amino acid sequence of PKKLRP (SEQ ID NO: 2). In some embodiments, the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof. In some embodiments, the peptide comprises N-terminal carboxylation, C-terminal amidation, one or more halogens, or a combination thereof. In some embodiments, the peptide is cyclized.

Provided herein, in another aspect, are methods of treating a neurodevelopmental disorder in a subject in need thereof, comprising administering to the subject a therapeutically effective amount of a peptide having a length of 7 amino acids to 20 amino acids and comprising an amino acid sequence of PKKLRP (SEQ ID NO: 2). In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof. In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome. In some embodiments, the motor disorders are developmental coordination disorder or stereotypic movement disorder. In some embodiments, the peptide comprises N-terminal carboxylation, C-terminal amidation, one or more halogens, or a combination thereof. In some embodiments, the peptide is cyclized.

Provided herein, in another aspect, are methods of treating Phelan-McDermid Syndrome in a subject in need thereof, comprising administering to the subject a therapeutically effective amount of a peptide having a length of 7 amino acids to 20 amino acids and comprising an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, are methods of treating depression in a subject in need thereof, comprising administering to the subject a therapeutically effective amount of a peptide consisting of an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, are methods of treating a central nervous system disorder in a subject in need thereof, comprising administering to the subject a therapeutically effective amount of a peptide consisting of an amino acid sequence of PKKLRP (SEQ ID NO: 2). In some embodiments, the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof. In some embodiments, the peptide comprises N-terminal carboxylation, C-terminal amidation, one or more halogens, or a combination thereof. In some embodiments, the peptide is cyclized.

Provided herein, in another aspect, are methods of treating a neurodevelopmental disorder in a subject in need thereof, comprising administering to the subject a therapeutically effective amount of a peptide consisting of an amino acid sequence of PKKLRP (SEQ ID NO: 2). In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof. In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome. In some embodiments, the motor disorders are developmental coordination disorder or stereotypic movement disorder. In some embodiments, the peptide comprises N-terminal carboxylation, C-terminal amidation, one or more halogens, or a combination thereof. In some embodiments, the peptide is cyclized.

Provided herein, in another aspect, are methods of treating Phelan-McDermid Syndrome in a subject in need thereof, comprising administering to the subject a therapeutically effective amount of a peptide consisting of an amino acid sequence of PKKLRP (SEQ ID NO: 2). In some embodiments, the peptide comprises N-terminal carboxylation, C-terminal amidation, one or more halogens, or a combination thereof. In some embodiments, the peptide is cyclized.

Provided herein, in another aspect, are methods of treating depression in a subject in need thereof, comprising administering to the subject a therapeutically effective amount of a peptide having a length of 7 amino acids to 20 amino acids and comprising an amino acid sequence having at least 65% sequence identity to SEQ ID NO: 2. In some embodiments, the peptide comprises an amino acid sequence having at least 85% sequence identity to SEQ ID NO: 2. In some embodiments, the peptide comprises N-terminal carboxylation, C-terminal amidation, one or more halogens, or a combination thereof. In some embodiments, the peptide is cyclized.

Provided herein, in another aspect, are methods of treating a central nervous system disorder in a subject in need thereof, comprising administering to the subject a therapeutically effective amount of a peptide having a length of 7 amino acids to 20 amino acids and comprising an amino acid sequence having at least 65% sequence identity to SEQ ID NO: 2. In some embodiments, the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof. In some embodiments, the peptide comprises N-terminal carboxylation, C-terminal amidation, one or more halogens, or a combination thereof. In some embodiments, the peptide is cyclized.

Provided herein, in another aspect, are methods of treating a neurodevelopmental disorder in a subject in need thereof, comprising administering to the subject a therapeutically effective amount of a peptide having a length of 7 amino acids to 20 amino acids and comprising an amino acid sequence having at least 65% sequence identity to SEQ ID NO: 2. In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof. In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome. In some embodiments, the motor disorders are developmental coordination disorder or stereotypic movement disorder. In some embodiments, the peptide comprises N-terminal carboxylation, C-terminal amidation, one or more halogens, or a combination thereof. In some embodiments, the peptide is cyclized.

Provided herein, in another aspect, are methods of treating Phelan-McDermid Syndrome in a subject in need thereof, comprising administering to the subject a therapeutically effective amount of a peptide having a length of 7 amino acids to 20 amino acids and comprising an amino acid sequence having at least 65% sequence identity to SEQ ID NO: 2. In some embodiments, the peptide comprises N-terminal carboxylation, C-terminal amidation, one or more halogens, or a combination thereof. In some embodiments, the peptide is cyclized.

Provided herein, in another aspect, are methods of treating depression in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids. In some embodiments, the fragment further comprises N-terminal carboxylation, C-terminal amidation, one or more halogens, or a combination thereof. In some embodiments, the fragment is cyclized.

Provided herein, in another aspect, are methods of treating a central nervous system disorder in a subject in need thereof, comprising administering to the subject a therapeutically effective amount an isolated fragment of a peptide, wherein the peptide consists of an amino acid sequence of SEQ ID NO: 2, and the fragment has a length of 3-5 amino acids. In some embodiments, the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof. In some embodiments, the fragment further comprises N-terminal carboxylation, C-terminal amidation, one or more halogens, or a combination thereof. In some embodiments, the fragment is cyclized.

Provided herein, in another aspect, are methods of treating a neurodevelopmental disorder in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids. In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof. In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome. In some embodiments, the motor disorders are developmental coordination disorder or stereotypic movement disorder. In some embodiments, the fragment further comprises N-terminal carboxylation, C-terminal amidation, one or more halogens, or a combination thereof. In some embodiments, the fragment is cyclized.

Provided herein, in another aspect, are methods of treating Phelan-McDermid Syndrome in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids. In some embodiments, the fragment further comprises N-terminal carboxylation, C-terminal amidation, one or more halogens, or a combination thereof. In some embodiments, the fragment is cyclized.

1 hr before the 5 min test session. Animals received a single 15 min Porsolt habituation session on the day before testing. N=7 rats/group.

Figure 2:
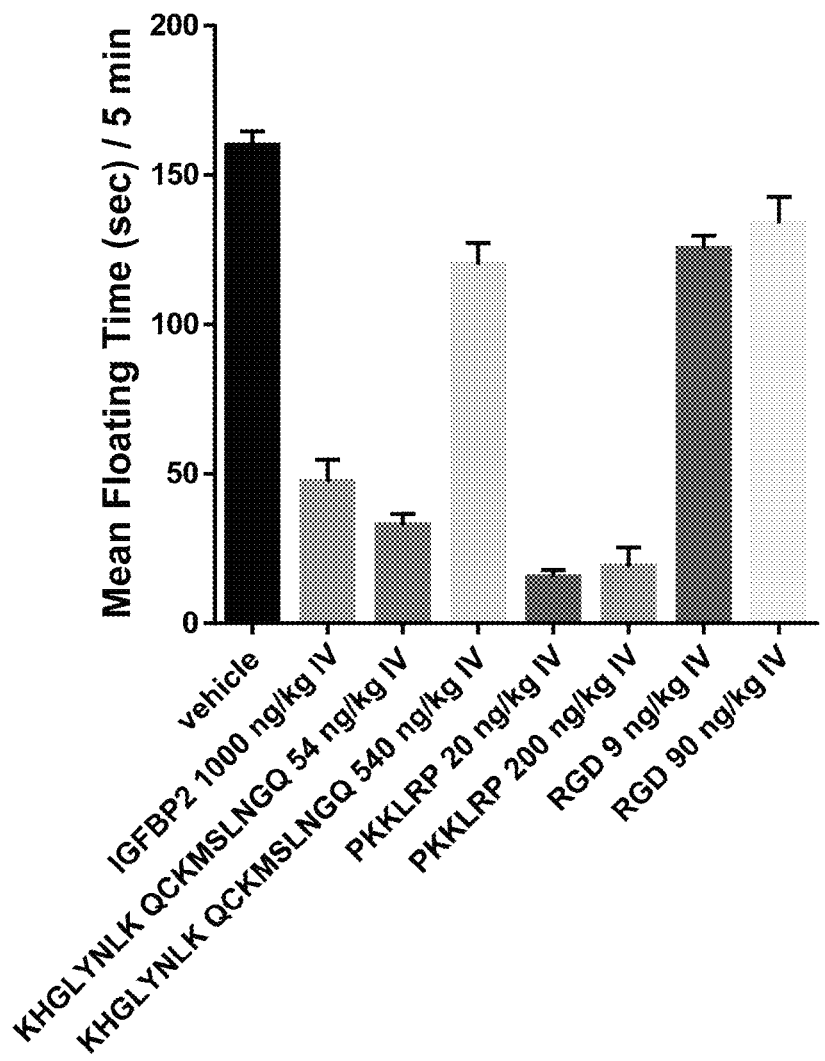

FIG. 2 demonstrates that IGFBP peptide fragments KHG-LYNLKQCKMSLNGQ (SEQ ID NO: 1) and PKKLRP (SEQ ID NO: 2) produce an equivalent antidepressant-like effect as IGFBP2 in the Porsolt test 1 hr post-dosing. Mean±SEM floating time in 2-3 month old male SD rats dosed with IGFBP peptide fragments, the positive control IGFBP2 or sterile saline vehicle (1 ml/kg) 1 hr before the 5 min test session. Animals received a single 15 min Porsolt habituation session on the day before testing. N=8 rats/group.

Figure 3A:
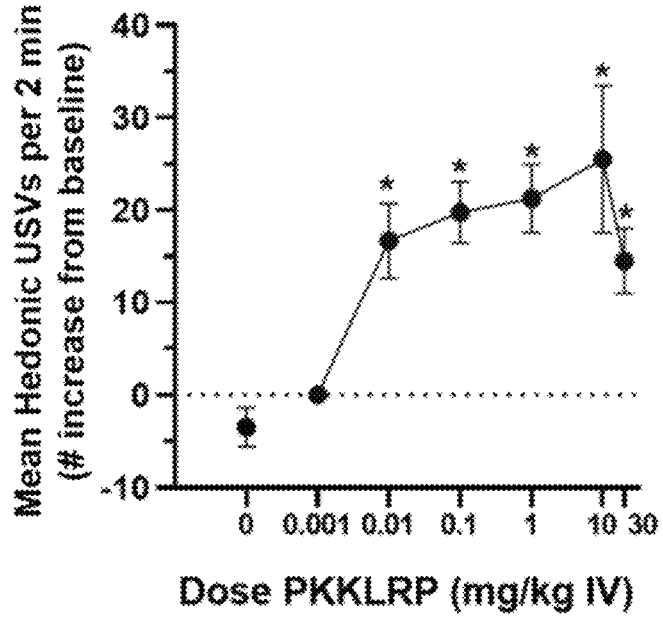
Figure 3B:
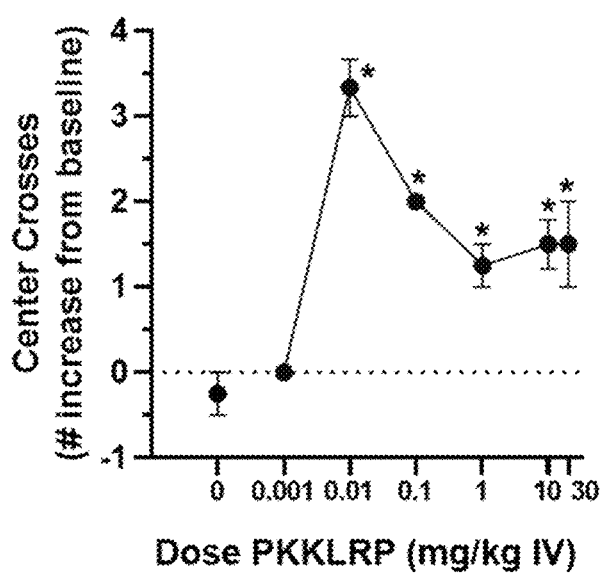

FIGS. 3A, 3B, 3C and 3D demonstrate assessment of PKKLRP (SEQ ID NO: 2) in rat models of Post-traumatic Stress Disorder (PTSD). FIG. 3A demonstrates positive emotional learning 1 hr post dosing in rats as measured by hedonic 50-kHz ultrasonic vocalizations (USVs) per every 2 minutes, such USVs occurring in response to a conditioned stimuli that predicts heterospecific play. FIG. 3B demonstrates number of center crosses, and index of an anxiolytic drug effect relevant to PTSD.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "peptide" refers to a polymer of amino acid residues joined by amide linkages, which may optionally be chemically modified to achieve desired characteristics. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include unnatural amino acids or residues contained in the group consisting of homocysteine, 2-Aminoadipic acid, N-Ethylasparagine, 3-Aminoadipic acid, Hydroxylysine, β-alanine, β-Aminopropionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

As used herein, "subject" refers to an animal, such as a mammal (including a human), that has been or will be the object of treatment, observation or experiment. "Subject" and "patient" may be used interchangeably, unless otherwise indicated. Mammals include, but are not limited to, mice, rodents, rats, simians, humans, farm animals, dogs, cats, sport animals, and pets. The methods described herein may be useful in human therapy and/or veterinary applications. In some embodiments, the subject is a mammal. In some embodiments, the subject is a human.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or caregiver.

The term "treatment" or "treating" means administering a compound disclosed herein for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are described herein.

Autism Spectrum Disorders

One in 59 children in the U.S. are diagnosed with autism spectrum disorder (ASD). Phelan-McDermid Syndrome (PMS) is an etiologically-defined form of ASD caused by loss of function of the Shank3 gene and is estimated to account for up to 2% of ASD diagnoses. Currently, there are no disease-modifying treatments for ASD or for PMS. Diverse clinical and developmental symptoms of PMS and ASD are managed through a host of expensive interventions with varying degrees of success. Due to the immense etiological heterogeneity, development of therapeutics for ASD is extremely challenging. However, drug development for etiologically-defined subtypes of ASD, such as PMS, could be achievable, and could pave the way for treatment of other forms of autism.

With the high prevalence of ASD diagnoses among the general population, and with over 80% co-occurrence with other developmental, neurologic, genetic and psychiatric diagnoses, the economic and social burden of the disease is enormous. The annual costs for children with ASD in the U.S. have been estimated to be $11.5-$60.9B (Lavelle et al., Pediatrics, (2014), 133(3):e520-529; Buescher et al., JAMA Pediatr., (2014), 168(8):721-728) Children and adolescents with ASD have median annual medical expenditures exceeding those of typically developing peers by a factor of 8.0-10.0×.

Phelan-McDermid Syndrome is a rare and complex neurodevelopmental disorder characterized by global developmental delay, variable degrees of intellectual disability (ID), absent or delayed speech, ASD, epilepsy, sensory processing, attention and motor deficits, hypotonia, regression, brain abnormalities, mild dysmorphic features, feeding and gastrointestinal problems, and a range of other co-morbid clinical conditions (Drapeau et al., eNeuro, (2018), 5(3): ENEURO.0046-18.2018; Harony-Nicolas et al., J. Child. Neurol., (2015), 30(14):1861-1870; Kolevzon et al., Mol. Autism, (2014), 5(1):54). Indeed, PMS is one of the most frequent and penetrant monogenic causes of autism and ID, representing up to 2% of cases of ASD (Leblond et al., PloS Genet., (2014), 10(9):e1004580). Development of the first effective pharmacological treatment for PMS would thus have an impact for the management of PMS and, potentially, ASD.

Insulin-Like Growth Factor Binding Protein (IGFBP)

Insulin-like growth factors (IGFs) are key growth-promoting peptides that act as both endocrine hormones and autocrine/paracrine growth factors. In the bloodstream and in local tissues, most IGF molecules are bound by one of the members of the IGF-binding protein (IGFBP) family.

IGFBPs 1-7 range in mass from ~22 to 29 kDA (213-289 amino acid length) and share a similar structure. These binding proteins have highly conserved N- and C-domains, each of which contain internal disulfide links. (See, e.g., www.peprotech.com)

Peptides

In one aspect, provided herein is an isolated peptide fragment of an insulin-like growth factor binding protein (IGFBP).

In another aspect, provided herein is an isolated peptide fragment of IGFBP2.

In another aspect, provided herein is an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein is an isolated peptide consisting of an amino acid sequence of KHG-LYNLKQCKMSLNGQ (SEQ ID NO: 1).

In another aspect, provided herein is an isolated peptide consisting of an amino acid sequence of KHG-LYNLKQCKMSLNGQ (SEQ ID NO: 1), or an isolated fragment thereof.

In another aspect, provided herein is an isolated fragment of a peptide, wherein the peptide consists of an amino acid sequence of SEQ ID NO:1, and the fragment has a length of 4-16 amino acids. In some embodiments, the fragment is cyclized.

In another aspect, provided herein is an isolated peptide comprising an amino acid sequence of SEQ ID NO:1, or an isolated fragment thereof, wherein the peptide or fragment has a length of 4-18 amino acids and is cyclized.

In another aspect, provided herein is an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. This includes 85, 86, 87, 88, 89, 90, 91, 92, 93, 94, 95, 96, 97, 98, or 99% sequence identity to SEQ ID NO: 1.

In another aspect, provided herein is an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 90% sequence identity to SEQ ID NO: 1.

In another aspect, provided herein is an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 95% sequence identity to SEQ ID NO: 1.

In another aspect, provided herein is an isolated peptide consisting of an amino acid sequence of PKKLRP (SEQ ID NO: 2).

In another aspect, provided herein is an isolated peptide consisting of an amino acid sequence of PKKLRP (SEQ ID NO: 2), or an isolated fragment thereof.

In another aspect, provided herein is an isolated fragment of a peptide, wherein the peptide consists of an amino acid sequence of SEQ ID NO:2, and the fragment has a length of 3-5 amino acids. In some embodiments, the fragment is cyclized.

In another aspect, provided herein is an isolated peptide comprising an amino acid sequence of SEQ ID NO:2, or an isolated fragment thereof, wherein the peptide or fragment has a length of 3-7 amino acids and is cyclized.

In another aspect, provided herein is an isolated peptide having a length of 7 amino acids to 8, 9, 10, 11, 12, 13, 14, 15, 16, 17, 18, 19, or 20 amino acids, comprising an amino acid sequence having at least 65% sequence identity to SEQ ID NO: 2.

In another aspect, provided herein is an isolated peptide having a length of 7 amino acids to 8, 9, 10, 11, 12, 13, 14, 15, 16, 17, 18, 19, or 20 amino acids, comprising an amino acid sequence having at least 85% sequence identity to SEQ ID NO: 2.

In some embodiments, the peptide disclosed herein comprises D- and L-amino acids. In some embodiments, the peptide disclosed herein comprises only L-amino acids.

In some embodiments, the peptide disclosed herein is cyclized. In some embodiments, the peptide disclosed herein is not cyclized.

In some embodiments, the peptide disclosed herein further comprises modifications on the N-terminus, the C-terminus, or both. For example, in one embodiment, the peptide further comprises an acyl group (such as, but not limited to, an acetyl group) on the N-terminus. In another embodiment, the peptide further comprises an amido group on the C-terminus.

In some embodiments, the peptide disclosed herein includes any form of a peptide having substantial homology to SEQ ID NO: 1 or SEQ ID NO: 2. In some embodiments, a peptide which is "substantially homologous" is about 50% homologous, more preferably about 70% homologous, even more preferably about 80% homologous, more preferably about 90% homologous, even more preferably, about 95% homologous, and even more preferably about 99% homologous to SEQ ID NO: 1 or SEQ ID NO:2.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

In some embodiments, a peptide disclosed herein is a variant comprising one or more deletions relative to a reference amino acid sequence. A "deletion" refers to a change in the amino acid or nucleotide sequence that results in the absence of one or more amino acid residues or nucleotides relative to a reference sequence. A deletion removes at least 1, 2, 3, 4, 5, 6, 7, 8, 9, 10, 11, 12, 13, 14, or 15 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

In some embodiments, a peptide disclosed herein is a variant comprising a fragment of a reference amino acid sequence. A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 4, 5, 6, 7, 8, 9, 10, 11, 12, 13, 14, 15, or 16 contiguous amino acid residues of a reference peptide, respectively. Fragments may be preferentially selected from certain regions of a molecule. The term "at least a fragment" encompasses the full length polynucleotide or full length polypeptide.

In some embodiments, a peptide disclosed herein is a variant comprising one or more insertions or additions relative to a reference sequence. The words "insertion" and "addition" refer to changes in an amino acid or sequence resulting in the addition of one or more amino acid residues. An insertion or addition may refer to 1, 2, 3, 4, 5, 6, 7, 8, 9, 10, 11, 12, 13, 14, 15, 16, 17, 18, 19, or 20 amino acid residues.

The peptides disclosed herein may be variants comprising one or more unnatural amino acids formed by post-translational modification or by introducing one or more unnatural amino acids during translation or during chemical synthesis. A variety of approaches are available for introducing unnatural amino acids during protein translation.

The peptides disclosed herein may be variants comprising one or more selected from halogens, optional substitutions with $C_1$-$C_3$ alkyl (further optionally substituted with one or more halogen or amino ($NH_2$) groups, or a combination thereof), optional substitutions with hydroxyl groups, optional substitutions with amino ($NH_2$) groups, and optional deletions of one or more of alkyl, hydroxyl, or amino groups. The variants comprising one or more halogens may include at least one radioactive isotopic halogen, such as 18-Fluorine.

A peptide of the present invention may be synthesized by any technique known to those of skill in the art and by methods as disclosed herein. Methods for synthesizing the disclosed peptides may include chemical synthesis of proteins or peptides, the expression of peptides through standard molecular biological techniques, and/or the isolation of proteins or peptides from natural sources. The disclosed peptides thus synthesized may be subject to further chemical and/or enzymatic modification. Various methods for commercial preparations of peptides and polypeptides are known to those of skill in the art.

A peptide of the present invention may alternatively be made by recombinant means or by cleavage from a longer polypeptide. The composition of a peptide may be confirmed by amino acid analysis or sequencing.

The peptides of the present invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides disclosed herein may be modified to include non-amino acid moieties. Modifications may include but are not limited to carboxylation (e.g., N-terminal carboxylation via addition of a di-carboxylic acid having 4-7 straight-chain or branched carbon atoms, such as glutaric acid, succinic acid, adipic acid, and 4,4-dimethylglutaric acid), amidation (e.g., C-terminal amidation via addition of an amide or substituted amide such as alkylamide or dialkylamide), PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), and benzylation (e.g., replacement of a hydrogen atom with a benzyl group). In some embodiments, proline is replaced with 2-amino-thiophene-3-carboxylate (Nadimpally et al., Chemistry Select, (2017), 3594-3596). In some embodiments, a benzene ring on select amino acid residue(s) is modified to include one or more fluorine atoms. In further embodiments, at least one of the fluorine atoms is 18-Fluorine.

Compositions

In some embodiments, a peptide described herein is formulated as a pharmaceutically acceptable composition when combined with at least one pharmaceutically acceptable carrier and/or excipient. Such pharmaceutically acceptable carrier(s) and/or excipient(s) are non-toxic and do not interfere with the efficacy of active ingredient (e.g., the peptides disclosed herein). The precise nature of the pharmaceutically acceptable carrier(s) and/or excipient(s) depends on the route of administration. The compositions can be formulated for any pharmaceutically acceptable route of administration, such as for example, by oral, parenteral, pulmonary, topical, rectal, nasal, vaginal administration, or via implanted reservoir. Parenteral or systemic administration includes, but is not limited to, subcutaneous, intravenous, intraperitoneally, intramuscular, intra-articular, intrasynovial, intrasternal, intrathecal, intralesional and intracranial injections. The compositions disclosed herein may be formulated into preparations in solid, semi-solid, liquid or gaseous forms, such as tablets, capsules, powders, granules, ointments, solutions, suppositories, injections, inhalants and aerosols.

In pharmaceutical dosage forms, the peptide disclosed herein may be administered in the form of its pharmaceutically acceptable salt (such as, but not limited to, an acetate salt) and/or as a pharmaceutically acceptable solvate of the salt thereof or of the free base form thereof, or the peptide may also be used alone or in appropriate association, as well as in combination, with other pharmaceutically active compounds. The following methods and excipients are merely exemplary and are in no way limiting.

For oral administration, liquid or solid dose formulations may be used. Some non-limiting examples of oral dosage formulations include tablets, gelatin capsules, pills, troches, elixirs, suspensions, syrups, wafers, chewing gum and the like. The peptide can be mixed with a suitable pharmaceutical carrier (vehicle) or excipient as understood by practitioners in the art. Non-limiting examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intrathecal, topical, intranasal, subcutaneous, or transdermal administration, formulations of the peptides useful in the methods of the present invention may utilize conventional diluents, carriers, or excipients etc., such as are known in the art can be employed to deliver the peptides. For example, the formulations may comprise one or more of the following: a stabilizer, a surfactant (such as a nonionic, ionic, anionic, cationic, or zwitterionic surfactant), and optionally a salt and/or a buffering agent. The peptide may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, mannitol, sorbitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the peptides useful in the methods of the present invention may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The amount of any individual excipient in the composition will vary depending on the role of the excipient, the dosage requirements of the active agent components, and particular needs of the composition. Generally, however, the excipient will be present in the composition in an amount of about 1% to about 99% by weight, from about 5% to about 98% by weight, or from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

In another aspect, provided herein are formulations comprising, consisting essentially of, or consisting of a peptide disclosed herein and at least one pharmaceutically acceptable excipient for intravenous, intramuscular, subcutaneous, or intranasal administration. In some embodiments, the formulation is for intravenous administration. In some embodiments, the formulation is for intramuscular administration. In some embodiments, the formulation is for subcutaneous administration. In some embodiments, the formulation is for intranasal administration.

One or more additional active agents may be administered with a peptide disclosed herein, either sequentially or concomitantly. In some embodiments, the peptide disclosed herein and the one or more additional active agents are administered within a single composition. Non-limiting examples of additional active agents include sodium chloride and carboxymethyl cellulose.

In some embodiments, a peptide disclosed herein can be administered to a patient in an effective amount ranging from about 0.1 mg/kg to about 500 mg/kg per day. This includes 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/kg.

Generally, a therapeutically effective amount of a peptide disclosed herein will range from a total daily dosage of about 0.1 mg/day to 500 mg/day, about 1-25 mg/day, about 3-15 mg/day, about 3-20 mg/day, about 30-720 mg/day, about 60-600 mg/day, or about 100-480 mg/day, or more. In some embodiments, a therapeutically effective amount of a peptide disclosed herein will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of a peptide disclosed herein is at least 0.1 mg/day, at least 0.5 mg/day, at least 1 mg/day, at least 5 mg/day, at least 10 mg/day, at least 15 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, or at least 500 mg/day.

Of course, the dosage may be changed according to the patient's age, weight, susceptibility, symptom, or the efficacy of the compound.

The peptides and compositions disclosed herein may be used to prepare formulations and medicaments that treat depression, central nervous system disorders, or neurodevelopmental disorders. In some embodiments, the peptides and compositions disclosed herein are used to prepare formulations and medicaments that treat autism spectrum disorders. In some embodiments, the peptides and compositions disclosed herein are used to prepare formulations and medicaments that treat Phelan-McDermid Syndrome.

Methods

In another aspect, provided herein are methods of treating depression in a subject in need thereof, the methods comprising, consisting essentially of, or consisting of administering to the subject a therapeutically effective amount of a peptide or a composition disclosed herein.

In another aspect, provided herein are methods of treating depression in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein are methods of treating depression in a subject in need thereof, the methods comprising, consisting essentially of, or consisting of administering to the subject a therapeutically effective amount of an isolated peptide consisting of an amino acid sequence of KHGLYNLKQCKMSLNGQ (SEQ ID NO: 1).

In another aspect, provided herein are methods of treating depression in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. In some embodiments, the amino acid sequence having at least 90% sequence identity to SEQ ID NO: 1. In some embodiments, the amino acid sequence having at least 95% sequence identity to SEQ ID NO: 1.

In another aspect, provided herein are methods of treating depression in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence of PKKLRP (SEQ ID NO: 2).

In another aspect, provided herein are methods of treating depression in a subject in need thereof, the methods comprising, consisting essentially of, or consisting of administering to the subject a therapeutically effective amount of a peptide consisting of an amino acid sequence of PKKLRP (SEQ ID NO: 2).

In another aspect, provided herein are methods of treating depression in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence having at least 65% sequence identity to SEQ ID NO: 2. In some embodiments, the amino acid sequence has at least 85% sequence identity.

In another aspect, provided herein are methods of treating a central nervous system disorder in a subject in need thereof, the methods comprising, consisting essentially of, or consisting of administering to the subject a therapeutically effective amount of a peptide or a composition disclosed herein. In some embodiments, the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

In another aspect, provided herein are methods of treating a central nervous system disorder in a subject in need thereof, the methods comprising, consisting essentially of, or consisting of administering to the subject a therapeutically effective amount of a peptide or a composition disclosed herein. In some embodiments, the central nervous system disorder is selected from autism spectrum disorders, bipolar disorder, catalepsy, depression, post-traumatic stress disorder (PTSD), encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

In another aspect, provided herein are methods of treating a central nervous system disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein are methods of treating a central nervous system disorder in a subject in need thereof, the methods comprising, consisting essentially of, or consisting of administering to the subject a therapeutically effective amount of an isolated peptide consisting of an amino acid sequence of KHGLYNLKQCKMSLNGQ (SEQ ID NO: 1).

In another aspect, provided herein are methods of treating a central nervous system disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. In some embodiments, the amino acid sequence having at least 90% sequence identity to SEQ ID NO: 1. In some embodiments, the amino acid sequence having at least 95% sequence identity to SEQ ID NO: 1.

In another aspect, provided herein are methods of treating central nervous system disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence of PKKLRP (SEQ ID NO: 2).

In another aspect, provided herein are methods of treating central nervous system disorder in a subject in need thereof, the methods comprising, consisting essentially of, or consisting of administering to the subject a therapeutically effective amount of a peptide consisting of an amino acid sequence of PKKLRP (SEQ ID NO: 2).

In another aspect, provided herein are methods of treating central nervous system disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence having at least 65% sequence identity to SEQ ID NO: 2. In some embodiments, the amino acid sequence has at least 85% sequence identity.

In another aspect, provided herein are methods of treating a neurodevelopmental disorder in a subject in need thereof, the methods comprising, consisting essentially of, or consisting of administering to the subject a therapeutically effective amount of a peptide or a composition disclosed herein. In some embodiments, the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

In another aspect, provided herein are methods of treating a neurodevelopmental disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein are methods of treating a neurodevelopmental disorder in a subject in need thereof, the methods comprising, consisting essentially of, or consisting of administering to the subject a therapeutically effective amount of an isolated peptide consisting of an amino acid sequence of KHGLYNLKQCKMSLNGQ (SEQ ID NO: 1).

In another aspect, provided herein are methods of treating a neurodevelopmental disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. In some embodiments, the amino acid sequence having at least 90% sequence identity to SEQ ID NO: 1. In some embodiments, the amino acid sequence having at least 95% sequence identity to SEQ ID NO: 1.

In another aspect, provided herein are methods of treating a neurodevelopmental disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence of PKKLRP (SEQ ID NO: 2).

In another aspect, provided herein are methods of treating a neurodevelopmental disorder in a subject in need thereof, the methods comprising, consisting essentially of, or consisting of administering to the subject a therapeutically effective amount of a peptide consisting of an amino acid sequence of PKKLRP (SEQ ID NO: 2).

In another aspect, provided herein are methods of treating a neurodevelopmental disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence having at least 65% sequence identity to SEQ ID NO: 2. In some embodiments, the amino acid sequence has at least 85% sequence identity.

In some embodiments, the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

In some embodiments, the motor disorders are developmental coordination disorder or stereotypic movement disorder.

In another aspect, provided herein are methods of treating an autism spectrum disorder in a subject in need thereof, the methods comprising, consisting essentially of, or consisting of administering to the subject a therapeutically effective amount of a peptide or a composition disclosed herein. In some embodiments, the autism spectrum disorder is classical autism or Autistic Disorder. In some embodiments, the autism spectrum disorder is Asperger Syndrome. In some embodiments, the autism spectrum disorder is Childhood Disintegrative Disorder. In some embodiments, the autism spectrum disorder is Pervasive Developmental Disorder—Not Otherwise Specified (PDD-NOS). In some embodiments, the autism spectrum disorder is Fragile X Syndrome. In some embodiments, the autism spectrum disorder is Rett Syndrome. In some embodiments, the autism spectrum disorder is Kanner syndrome. In some embodiments, the autism spectrum disorder is Phelan-McDermid Syndrome.

In another aspect, provided herein are methods of treating an autism spectrum disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein are methods of treating an autism spectrum disorder in a subject in need thereof, the methods comprising, consisting essentially of, or consisting of administering to the subject a therapeutically effective amount of an isolated peptide consisting of an amino acid sequence of KHGLYNLKQCKMSLNGQ (SEQ ID NO: 1).

In another aspect, provided herein are methods of treating an autism spectrum disorder in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. In some embodiments, the amino acid sequence having at least 90% sequence identity to SEQ ID NO: 1. In some embodiments, the amino acid sequence having at least 95% sequence identity to SEQ ID NO: 1.

In another aspect, provided herein are methods of treating an autism spectrum disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence of PKKLRP (SEQ ID NO: 2).

In another aspect, provided herein are methods of treating an autism spectrum disorder in a subject in need thereof, the methods comprising, consisting essentially of, or consisting of administering to the subject a therapeutically effective amount of a peptide consisting of an amino acid sequence of PKKLRP (SEQ ID NO: 2).

In another aspect, provided herein are methods of treating an autism spectrum disorder in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence having at least 65% sequence identity to SEQ ID NO: 2. In some embodiments, the amino acid sequence has at least 85% sequence identity.

In another aspect, provided herein are methods of treating Phelan-McDermid Syndrome in a subject in need thereof, the methods comprising, consisting essentially of, or consisting of administering to the subject a therapeutically effective amount of a peptide or a composition disclosed herein.

In another aspect, provided herein are methods of treating Phelan-McDermid Syndrome in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence of KHGLYNLKQCKMSLNGQ (SEQ ID NO: 1).

In another aspect, provided herein are methods of treating Phelan-McDermid Syndrome in a subject in need thereof, the methods comprising, consisting essentially of, or consisting of administering to the subject a therapeutically effective amount of an isolated peptide consisting of an amino acid sequence of KHGLYNLKQCKMSLNGQ (SEQ ID NO: 1).

In another aspect, provided herein are methods of treating Phelan-McDermid Syndrome in a subject in need thereof, the methods comprising, consisting essentially of, or consisting of administering to the subject a therapeutically effective amount of an isolated peptide having a length of 18 amino acids to 19, 20, 21, 22, 23, 24, 25, 26, 27, 28, 29, 30, 31, 32, 33, 34, 35, 36, 37, 38, 39, or 40 amino acids, comprising an amino acid sequence having at least 85% sequence identity to SEQ ID NO: 1. In some embodiments, the amino acid sequence having at least 90% sequence identity to SEQ ID NO: 1. In some embodiments, the amino acid sequence having at least 95% sequence identity to SEQ ID NO: 1.

In another aspect, provided herein are methods of treating Phelan-McDermid Syndrome in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence of PKKLRP (SEQ ID NO: 2).

In another aspect, provided herein are methods of treating Phelan-McDermid Syndrome in a subject in need thereof, the methods comprising, consisting essentially of, or consisting of administering to the subject a therapeutically effective amount of a peptide consisting of an amino acid sequence of PKKLRP (SEQ ID NO: 2).

In another aspect, provided herein are methods of treating Phelan-McDermid Syndrome in a subject in need thereof, the methods comprising, consisting essentially of, or consisting of administering to the subject a therapeutically effective amount of a peptide having a length of 7 amino acids to 8, 9, 10, 11, 12, 13, 14, 15, 16, 17, 18, 19, or 20 amino acids and comprising an amino acid sequence having at least 65% sequence identity to SEQ ID NO: 2. In some embodiments, the amino acid sequence has at least 85% sequence identity.

The present invention, thus generally described, will be understood more readily by reference to the following examples, which are provided by way of illustration and are not intended to be limiting of the present invention.

EXAMPLES

Animals

Adult male (2-3 month old) Sprague-Dawley (SD) rats were purchased from Harlan (USA) for the Porsolt Forced Swim Test. Rats were housed in Lucite cages with aspen wood chip bedding, maintained on a 12:12 light:dark cycle (lights on at 5 AM), and given ad libitum access to Purina lab chow (USA) and tap water throughout the study. All experiments were approved by the Sai Life Sciences (India) Animal Care and Use Committees.

Example 1

Porsolt Forced Swim Test

Porsolt forced swim testing was conducted as described in (Burgdorf et al., Neuropsychopharmacology, (2013), 38(5): 729-742). Rats were dosed with IGFBP1-7 (1 microgram/kg i.v.; peprotech, USA) (3 mg/kg, i.v.), ketamine (10 m/kg i.v.; Sigma, USA) or 0.9% sterile saline vehicle (1 ml/kg, i.v.). Injections were made in the lateral tail vein and rats were tested 1 hr post-dosing. Animals were placed in a 46 cm tall×20 cm in diameter clear glass tube filled to 30 cm with tap water (23±1° C.) for 15 min on the first day (habituation) and 5 min on the subsequent test day. Water was changed after every other animal. Animals were videotaped, and tapes were scored offline by a blind experimenter with high inter-rater reliability (Pearson's r>0.9). Floating time (sec) was defined as the minimal amount of effort required to keep the animal's head above and diving (number of incidences) was registered when the whole body of the animal was submersed and the animal's head was facing towards the bottom of the tank.

Figure 1A:
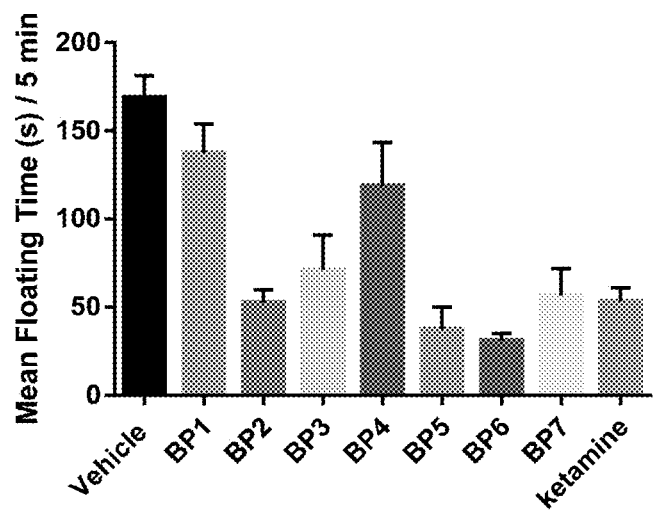
FIGS. 1A and 1B demonstrate that IGFBP2, IGFBP3, and IGFBP5 (1 µg/kg, i.v.) produce an equivalent antidepressant-like effect as ketamine in the Porsolt test 1 hr post-dosing without showing dissociative side effects as measured by diving behavior. Mean±SEM (FIG. 1A) floating time or (FIG. 1B) number of dives, barrel rolls, or odd behavior in the rat Porsolt test in 2-3 month old male SD rats dosed with IGFBP1-7 (1 µg/kg, i.v.), the positive control ketamine (10 mg/kg, i.v.) or sterile saline vehicle (1 ml/kg)
Figure 1B:
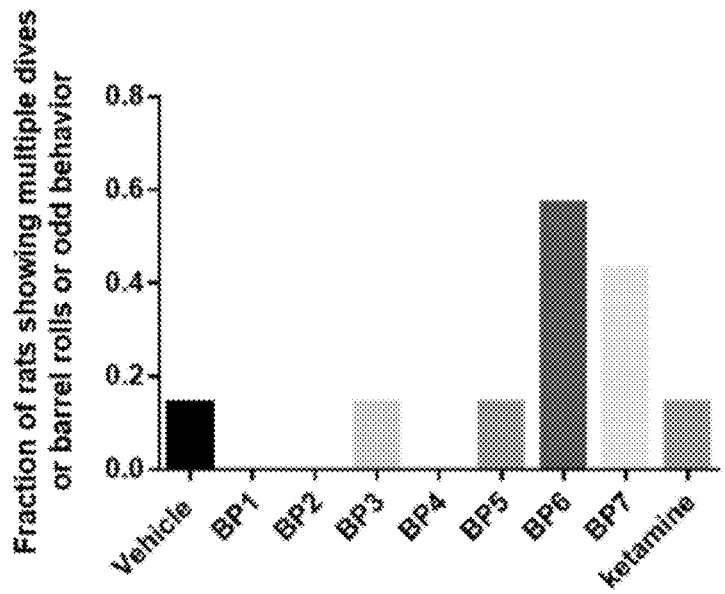

As shown in FIG. 1A, IGFBP2, IGFBP3, IGFBP5, IGFBP6, and IGFBP7 produced an equivalent antidepressant-like effect in the Porsolt Test as ketamine compared to saline vehicle as measured by floating time; $F(8, 54)=11.01$, $P<0.05$; Fisher's PLSD post hoc test IGFBP2, IGFBP3, IGFBP5, or IGFBP7 vs vehicle, $P<0.05$; and IGFBP2, IGFBP3, IGFBP5, or IGFBP 7 vs ketamine, $P>0.05$. As shown in FIG. 1B, IGFBP showed a greater percentage of animals that exhibited more than 1 dive per 5 min test session than vehicle, which is potentially indicative of dissociative/sedative side effects. Therefore, IGFB2, IGFBP3, and IGFBP5 show antidepressant-like effects equivalent to vehicle without dissociative/sedative side effects. The raw data is shown in Table 1.

TABLE 1

| Rat # | behavior | veh | BP1 | BP2 | BP3 | BP4 | BP5 | BP6 | BP7 | ket |
|---|---|---|---|---|---|---|---|---|---|---|
| 1 | floating | 193.9 | 67.5 | 41.6 | 42.8 | 175.7 | 55 | 10.9 | 52.5 | 79.5 |
| 2 | floating | 140.4 | 179.1 | 43.5 | 23.3 | 189.5 | 8.4 | 45 | 94.4 | 31.2 |
| 3 | floating | 161.2 | 130.7 | 25.7 | 84.9 | 59 | 27.7 | 27.2 | 9.8 | 59.3 |
| 4 | floating | 190.6 | 96.8 | 68.2 | 140.5 | 64.7 | 25.7 | 35.5 | 30.8 | 78.1 |
| 5 | floating | 136.8 | 187.9 | 83.6 | 142.3 | 172.9 | 27.7 | 36.3 | 60.1 | 39.6 |
| 6 | floating | 138.2 | 156.8 | 59.8 | 29.3 | 32.4 | 14.4 | 25.6 | 24.5 | 30.5 |
| 7 | floating | 220.4 | 143.4 | 45.5 | 35.8 | 137.2 | 104.6 | 36.6 | 123.8 | 55 |
| 1 | diving | 0 | 0 | 0 | 0 | 0 | 0 | 0 | 0 | 0 |
| 2 | diving | 1 | 0 | 0 | 0 | 0 | 0 | 0 | 1 | 0 |
| 3 | diving | 0 | 0 | 0 | 1 | 0 | 1 | 1 | 1 | 1 |
| 4 | diving | 0 | 0 | 0 | 0 | 0 | 0 | 1 | 1 | 0 |
| 5 | diving | 0 | 0 | 0 | 0 | 0 | 0 | 0 | 0 | 0 |
| 6 | diving | 0 | 0 | 0 | 0 | 0 | 0 | 1 | 0 | 0 |
| 7 | diving | 0 | 0 | 0 | 0 | 0 | 0 | 1 | 0 | 0 |

Example 2

Sequence Homology Mapping and Chemistry

Based on the results of the Porsolt test in Example 1, IGFBP2, IGFBP3, and IGFBP5 were identified as the best binding proteins for inducing robust antidepressant-like effects without side effects. Given the structural similarities between all 7 IGFBPs, an amino acid sequence homology was performed to identify sequences that were homologues between IGFBP2, IGFBP3, and IGFBP5 and were not consistently shared with IGFBP1, IGFBP6 and IGFBP7. Based on this analysis, three peptides were identified (KHGLYNLKQCKMSLNGQ (SEQ ID NO: 1); PKKLRP (SEQ ID NO: 2); RGD). These peptides were synthesized using standard solid phase peptide chemistry and were assessed in the Porsolt Test as described above.

As shown in FIG. 2, KHGLYNLKQCKMSLNGQ (SEQ ID NO: 1) (low dose), and PKKLRP (SEQ ID NO: 2) (low dose and high dose) produced an equivalent or superior antidepressant-like effect in the Porsolt test as IGFBP2 compared to saline vehicle as measured by floating time; $F(7, 56)=95.3$, $P<0.05$; Fisher's PLSD post hoc test vs vehicle, $P<0.05$; and vs IGFBP2, $P>0.05$. Diving behavior was not apparent in this experiment. The raw data is shown in Table 2.

TABLE 2

| Rat # | behavior | veh | BP2 | KH... 54 | KH... 540 | PK... 20 | PK... 200 | RGD 9 | RGD 90 |
|---|---|---|---|---|---|---|---|---|---|
| 1 | floating | 160.2 | 35.6 | 24.2 | 149.1 | 26.2 | 9 | 125.8 | 133.6 |
| 2 | floating | 172.4 | 28.2 | 43.3 | 101.5 | 18.2 | 18.4 | 108.2 | 81.6 |
| 3 | floating | 159 | 65.8 | 33.4 | 105.8 | 15.5 | 45.6 | 140.6 | 143.4 |
| 4 | floating | 166 | 44.3 | 53.8 | 130 | 22.4 | 2.3 | 139.7 | 149.6 |
| 5 | floating | 133.4 | 79.1 | 27.4 | 147.9 | 7.6 | 7.7 | 127.8 | 123.7 |
| 6 | floating | 157.1 | 37.2 | 29.2 | 108.7 | 16.6 | 17.3 | 115.4 | 137 |
| 7 | floating | 152 | 67.1 | 26.5 | 94.8 | 6.6 | 4.3 | 132.9 | 169 |
| 8 | floating | 178.2 | 22 | 25.2 | 121.4 | 10.2 | 47.8 | 113.1 | 132.7 |

Example 3

Comparison of Dendritic Spine Morphologies Between Shank3−/−, Shank3+/− Mice and Wild Type (WT) Controls Primary neuronal cultures from frontal cortices of E21 embryonic mice are generated and cultured in vitro for 28 days on poly-D-lysine (PDL)-laminin coated glass coverslips, fed with Neurobasal medium supplemented with 2% B27 Supplement, penicillin/streptomycin (100 U/mL and 100 mg/mL, respectively), and 2 mM GlutaMAX-I (see, e.g., Russell et al., Biol. Psychiatry, (2018), 83(6):499-508; Smith et al., Neuron, (2014), 84(2):399-415). Neurons are then transfected with a plasmid expressing enhanced Green Fluorescent Protein (eGFP) and after 2 days, treated with a peptide disclosed herein (e.g., KHGLYNLKQCKMSLNGQ (SEQ ID NO: 1) or PKKLRP (SEQ ID NO: 2)) suspended in media. Dose-response curves are generated for at least four concentrations of each peptide (1, 10, 100, 1000 nM), the positive control (IGFBP2, 1000 nM) or media. Treated neurons are fixed and stained with antibodies for GFP (Abcam) and anti-PSD95 (Antibodies Incorporated), followed by fluorescent Alexa Fluor 488 and Alexa Fluor 568 secondary antibodies (Invitrogen). Images of healthy GFP-positive pyramidal neurons are captured with a Zeiss LSM5 Pascal confocal microscope using a 63× oil-immersion objective (N.A. 1.4) and are reconstructed using MetaMorph (Molecular Devices). Dendritic spine morphometric analysis (area, length, width and linear density) is performed using MetaMorph. Cultures directly compared are stained simultaneously and are imaged with the same acquisition parameters. For each condition, 3-10 neurons each from 2-5 separate experiments are used. Experiments are performed blind to conditions.

Spine parameter data, such as spine size and density, is analyzed with GraphPad Prism by a one-way ANOVA, followed by Bonferroni correction for multiple comparisons. Comparisons between WT, Shank3−/− and Shank3+/− cultures are performed using a two-tailed unpaired t-test.

It is expected that Shank3−/− and Shank3+/− mice will have reduced spine sizes and linear densities. It is expected that a peptide disclosed herein (e.g., KHG-LYNLKQCKMSLNGQ (SEQ ID NO: 1) or PKKLRP (SEQ ID NO: 2)) administration will increase spine sizes and linear density.

Example 4

Determination of the Ability of a Peptide Disclosed Herein (e.g., KHGLYNLKQCKMSLNGQ (SEQ ID NO: 1) or PKKLRP (SEQ ID NO: 2)) to Rescue in Vivo Dendritic Spine Morphology and In Vivo Auditory LTP Deficits in Shank3-Deficient Mice Adult Shank3−/−, Shank3+/− and WT control mice are dosed with either a peptide disclosed herein (1, 10, 100, 1000 pg/kg, i.v.), the positive control (IGFBP2, 1000 pg/kg, i.v.) or sterile saline vehicle via lateral tail vein using the i.v. dosing protocol in mice published in Rajagopal et al. (Behav. Brain Res., (2016), 299:105-110). Vehicle dosed WT mice are used to determine the effect of Shank3 knockout on these phenotypes.

Dendritic Spine Morphology. Dendritic spine analyses are conducted as described in Burgdorf et al. (Neuroscience, (2015), 308:202-211). Twenty-four hours after dosing mice are transcardially perfused and the brains are processed for dendritic spine morphology quantification using ballistic dye labeling. Brains are sectioned using a tissue Vibratome (Leica VT1000) to collect 300 µm thick sections from the anterior to posterior extremes of each brain. Ballistic dye labeling (DiI and DiO coated on tungsten particles) are performed using a gene gun (Bio-Rad) to label target neurons. Laser-scanning confocal microscopy (Olympus FV1000) is performed using a 63× objective (1.42 NA). Microscopy is performed blind to experimental conditions. A minimum of 5 cells per animal is sampled. Medial prefrontal cortex (MPFC) samples (50 µm) are analyzed. Blind deconvolution (AutoQuant) is applied to raw 3-dimensional digital images. Individual spines are measured manually for head diameter, spine length, and spine neck diameter from image Z-stacks using software. An optimal dose for a particular peptide disclosed herein may be obtained through these studies and that dose used in the auditory LTP study described below. Secondary endpoints (non-tuff dendrites in pyramidal, as well as proximal and distal dentate in the dentate gyms) may also be used to determine the optimal dose.

Auditory LTP. Noninvasive methods for measuring synaptic plasticity via LTP in mice. Mice are anesthetized using isoflurane, and cortical EEG is implanted via skull screws (Pinnacle). Auditory evoked potentials are recorded from a frontal cortex skull screw using a cerebellar skull screw as a ground. EEG signals are captured via a tethered system (Pinnacle); auditory evoked potentials are recorded from frontal cortex skull screws using a cerebellum skull screw as a ground/reference. Data is acquired at 1,000 samples per second using an A&M amplifier with a high (0.1 Hz) and low pass (100 Hz) filters. Data is recorded using Data Wave acquisition software and is analyzed using Brain Products Analyzer 2 software. LTP is induced by an auditory tetanus (6-kHz, 50 ms in duration), presented 10 times per second for 5 min (total of 3,000 tones) using a similar paradigm as Clapp et al. (Eur. J. Neurosci., (2005), 22(5):1135-1140). Mismatch negativity testing occurs immediately before tetanus (pre-tetanus) and 1 hr after tetanus (post-tetanus) following a specific protocol. Post-pre tetanus difference waves are generated to determine the range (in milliseconds) in which LTP occurred. Secondary endpoints include mismatch negativity and quantitative EEG.

Data is analyzed using an ANOVA with each experimental group entered as an independent factor with Fisher PLSD post-hoc tests. α=0.05. The optimal dose of each peptide is to be defined as the lowest dose that (1) shows a significant effect compared to vehicle, (2) is not statistically inferior to higher doses, and (3) shows at least 85% of the maximal effect of the most effective dose. A post hoc test comparing the peptide(s) and vehicle is used to determine if the peptide(s) facilitated auditory LTP.

It is expected that the peptides disclosed herein will fully restore or at least significantly enhance spine density and auditory LTP in mice. The approach described above can be applied identically in rodent and human studies, as the same noninvasive auditory LTP method can be used in humans in future studies. Treatment regimens that reverse spine deficits and LTP in mice are expected to lead to behavioral improvements, as determined in Example 5 below.

Example 5

Determination of the Ability of Peptides Disclosed Herein to Rescue In Vivo Learning, Memory and Vocalization Quality Measures in Shank3-Deficient Mice This study measures novel object recognition (NOR) for memory, as well as home cage ultrasonic vocalizations (USVs) for speech in Shank3-deficient mice.

Adult Shank3−/−, Shank3+/− and WT control mice are dosed with a peptide disclosed herein (optimal dose determined in Example 3), the positive control (IGFBP2, 1000 pg/kg, i.v.) or sterile saline vehicle via lateral tail vein using the i.v. dosing protocol in mice described in Rajagopal et al. (Behav. Brain Res., (2016), 299:105-110).

Methods to measure NOR are described Rajagopal et al. (Behav. Brain Res., (2016), 299:105-110). The primary endpoint is the D2 discrimination index.

Methods for ultrasonic vocalization recording are described in Srivastava et al. (J. Neurosci., (2012), 32(34): 11864-11878). Heterospecific rough-and-tumble play is conducted, and testing occurs 3 hours post-dosing or 1 day after the last rough-and-tumble play session. The experimenter is blind to the treatment condition. High-frequency USVs are recorded and analyzed by sonogram in a blind manner as described in Burgdorf et al. (Neuroscience, (2011), 192:515-523). Animals are not habituated to play stimulation before dosing and testing. Rate of USVs, spectrographic properties of USVs, and social contact time are measured and the primary endpoint is rates of ultrasonic calls. An increase in 50-kHz USVs that occurs across trial blocks reflects positive emotional learning. Secondary endpoint measures of social contact time and sonographic features of USVs include loudness, peak frequency, and bandwidth.

Data is analyzed using an ANOVA with each experimental group entered as an independent factor with Fisher PLSD post-hoc tests α=0.05. A post hoc test comparing the peptide(s) and vehicle is used to determine if the peptide(s) affected the primary endpoints for the NOR or USV experiments.

It is expected that peptides disclosed herein will rescue or enhance at least one of these phenotypes.

Alternatively, behavioral learning was tested in trace eyeblink conditioning, Morris water maze, and/or alternating t-maze tasks as described in Burgdorf et al. (Neurobiol. Aging, (2011), 32(4):698-706). It is expected that peptides disclosed herein will enhance learning in all three tasks.

Example 6

Assessment of Sleep Slow Wave Activity (SWA) Parameters and Central Brain-Derived Neurotrophic Factor (BDNF) in Human Adult Subjects with Major Depressive Disorder (MDD)

Sleep SWA parameters and BDNF may serve as non-invasive indices for testing the efficacy of antidepressant therapy. Following an adaptation night, whole night sleep recordings are obtained for adult subjects (diagnosed with MDD without psychotic features) on the night before compound infusion as well as on the two following nights. The adult subjects are each administered a single intravenous infusion of compound (a peptide disclosed herein, e.g., KHGLYNLKQCKMSLNGQ (SEQ ID NO: 1) or PKKLRP (SEQ ID NO: 2)). Electroencephalogram (EEG) recordings are performed approximately 12 hours after compound infusion. Two EEGs (C3/A2 and C4/A1), two electrooculograms and one submental electromyogram are recorded. Slow wave parameters are calculated by applying a procedure adopting fixed parameters derived from sleep EEG standard guidelines (Reidner et al., Sleep, 2007, 1643-1657). BDNF is collected using a vacutainer system before compound infusion as well as 230 minutes after compound infusion. These blood samples are analyzed using an anti-BDNF sandwich ELISA kit.

Example 7

Assessment of Experience-Dependent Neuroplasticity in Healthy Human Adult Subjects In a randomized, double-blind study, healthy adult subjects receive a single dose of (a) a peptide disclosed herein (e.g., KHGLYNLKQCKMSLNGQ (SEQ ID NO: 1) or PKKLRP (SEQ ID NO: 2)) or (b) placebo. EEG testing begins 3 hours after compound or placebo administration, followed by cognitive testing. To explore potential delayed effects of compound on memory consolidation, adult subjects return to testing site to repeat the cognitive tasks. Adult subjects complete a visual long term potentiation (LTP) task using high-frequency visual stimulation (HFvS) to induce potentiation of visual cortex neurons, followed by a weather prediction task (WPT), an information integration task (IIT), and an n-back task (e.g., a spatial working memory task).

Example 8

Assessment in Rat Models of Post-Traumatic Stress Disorder (PTSD)

Figure 3C:
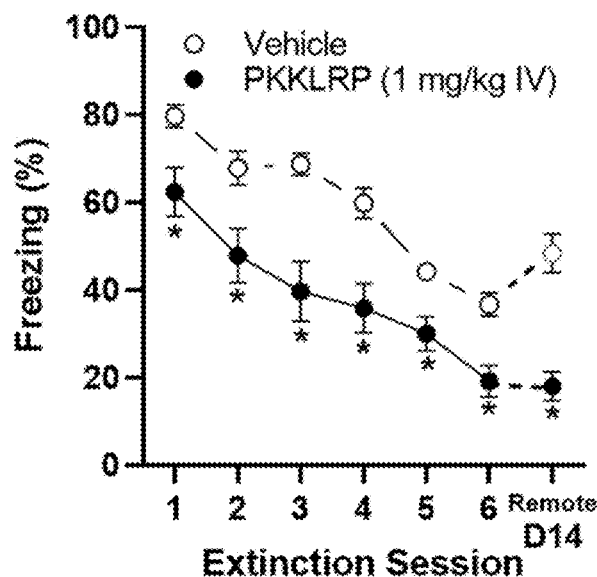
Figure 3D:
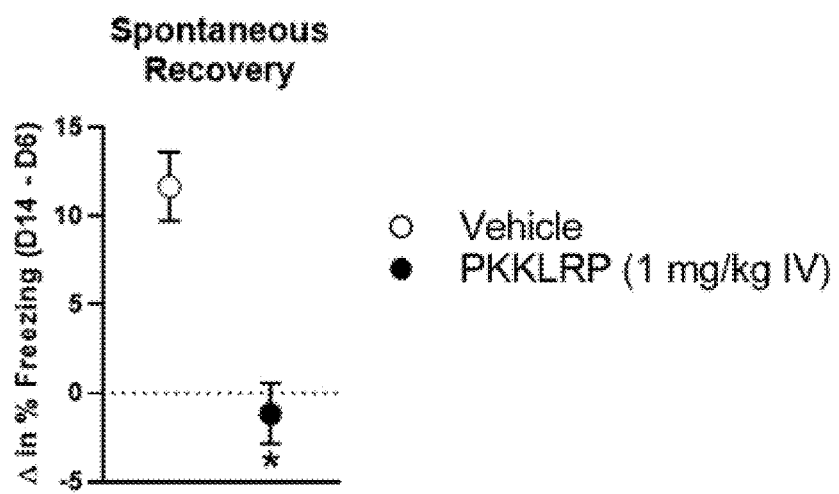

As shown in FIGS. 3A-3D, PKKLRP (SEQ ID NO: 2) increased positive emotional learning 1 hr post dosing in rats as measured by rates of hedonic ultrasonic vocalizations that occur during heterospecific play, which captures both pro-social and vocal learning relevant to autism [$F(1, 21)$=14.9, $P<0.05$; Fisher's PLSD post hoc test for 0.01, 0.1, 1, 10, and 30 mg/kg vs. vehicle, $P<0.05$; FIG. 3A)]. Center crosses, an index of an anxiolytic drug effect relevant to PTSD, were also increased across these same dose levels in the same assay [$F(1, 21)$=13.8, $P<0.05$; Fisher's PLSD post hoc test for 0.01, 0.1, 1, 10, and 30 mg/kg vs. vehicle, $P<0.05$; FIG. 3B)]. PKKLRP (SEQ ID NO: 2) at 1 mg/kg IV one hour before the first extinction session also increased contextual fear extinction (a well validated model of PTSD) across each test day [F(1, 10)=32.3, P<0.05; Fisher's PLSD post hoc test for session 1, 2, 3, 4, 5, and 6 for drug vs. vehicle, P<0.05; FIG. 3C)], as well as spontaneous recovery comparing the difference in freezing 14 days post dosing versus extinction session 6 [F(1, 10)=32.3, P<0.05; FIG. 3D]. These experiments were conducted as described in Burgdorf et al. (Int. J. Neuropsychopharmacol., 2017, 20:476-484).

Example 9

Human Clinical Trial for Phelan-McDermid Syndrome (PMS)

In a double-blind, placebo-controlled, crossover design trial, human subjects (confirmed to have SHANK3 deletions or mutations based on chromosomal microarray or high-throughput or targeted sequencing) are intravenously administered a peptide disclosed herein (e.g., KHGLYNLKQCKMSLNGQ (SEQ ID NO: 1) or PKKLRP (SEQ ID NO: 2)) over a period of three months and placebo over a period of three months in random order, separated by a 4-week washout period. Efficacy measurements are taken at baseline of each treatment phase, and at weeks 4, 8, and 12 of each treatment phase. Social impairment and restrictive behaviors were measured by the Aberrant Behavior Checklist and the Repetitive Behavior Scale, respectively.

Example 10

Human Clinical Trial for Obsessive-Compulsive Disorder (OCD)

In a randomized, double-blind, placebo-controlled, crossover design trial, drug-free OCD adult subjects with near-constant obsessions receive two intravenous infusions, one of saline and a peptide disclosed herein (e.g., KHGLYNLKQCKMSLNGQ (SEQ ID NO: 1) or PKKLRP (SEQ ID NO: 2)), spaced at least 1-week apart. The OCD visual analog scale (OCD-VAS) and the Yale-Brown Obsessive-Compulsive Scale (Y-BOCS) are used to assess OCD symptoms.

Example 11

Human Clinical Trial for Chronic Post-Traumatic Stress Disorder (PTSD)

In a randomized, double-blind crossover design trial with an active placebo control, adult subjects (free of concomitant psychotropic medications for 2 weeks prior to randomization for the duration of the study) receive two intravenous infusions of (a) a peptide disclosed herein (e.g., KHGLYNLKQCKMSLNGQ (SEQ ID NO: 1) or PKKLRP (SEQ ID NO: 2)) or (b) midazolam, spaced two weeks apart. Eligible adult subjects have a primary diagnosis of PTSD assessed with the Structured Clinical Interview for DSM-IV-TR Axis I Disorders-Patient Version and a score of at least 50 on the Clinician-Administered PTSD Scale (CAPS). The primary outcome is PTSD symptom severity 24 hours after infusion, assessed with the Impact of Event Scale-Revised (IES-R). Secondary outcome measures include the Montgomery-Asberg Depression Rating Scale (MADRS), the Quick Inventory of Depressive Symptomology, Self-Report (QIDS-SR), and the Clinical Global Impression-Severity (CGI-S) and -Improvement (GCI-I) scales administered by a study clinician 24 hours, 48 hours, 72 hours, and 7 days after infusion. The IES-R is also administered 48 hours, 72 hours, and 7 days after infusion. The CAPS is administered at baseline and 7 days after infusion. Patients who score 50 or higher on the CAPS 2 weeks after the first infusion receive an infusion of the second study drug. Patients whose symptoms remain significantly improved 2 weeks after infusion (indicated by a CAPS score of <50 at 2 weeks) are considered to have completed the study after 1 infusion.

Example 12

Human Clinical Trial for Treatment-Resistant Major Depression

In a randomized, placebo-controlled, double-blind crossover design trial, adult subjects (drug-free for two weeks prior to the study) receive an intravenous infusion of (a) a peptide disclosed herein (e.g., KHGLYNLKQCKMSLNGQ (SEQ ID NO: 1) or PKKLRP (SEQ ID NO: 2)) or (b) placebo on two test days, a week apart. Adult subjects are rated at baseline and at 40, 80, 110, and 230 minutes and 1, 2, 3, and 7 days post-infusion. Rating scales include the 21-item Hamilton Depression Rating Scale (HDRS) as the primary outcome measure, and the secondary outcome measures: The Beck Depression Inventory (BDI), Brief Psychiatric Rating Scale (BPRS) positive symptoms subscale, Young Mania Rating Scale (YMRS), and the visual analog scale.

While certain embodiments have been illustrated and described, it should be understood that changes and modifications can be made therein in accordance with ordinary skill in the art without departing from the present invention in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed invention. Additionally, the phrase "consisting essentially of" will be understood to include those elements specifically recited and those additional elements that do not materially affect the basic and novel characteristics of the claimed invention. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Para. A. An isolated peptide having a length of 18 amino acids to 40 amino acids, comprising an amino acid sequence of KHGLYNLKQCKMSLNGQ (SEQ ID NO: 1).

Para. B. An isolated peptide consisting of an amino acid sequence of KHGLYNLKQCKMSLNGQ (SEQ ID NO: 1), or an isolated fragment of the peptide.

Para. C. The peptide of Para. B, or the fragment thereof, wherein the fragment has a length of 4-16 amino acids.

Para. D. An isolated peptide having a length of 18 amino acids to 40 amino acids, comprising an amino acid sequence having at least 85% sequence identity to SEQ ID NO: 1.

Para. E. The peptide of Para. D comprising an amino acid sequence having at least 90% sequence identity to SEQ ID NO: 1.

Para. F. The peptide of Para. D comprising an amino acid sequence having at least 95% sequence identity to SEQ ID NO: 1.

Para. G. The peptide of any one of Paras. A-F, further comprising N-terminal carboxylation, C-terminal amidation, one or more halogens, or a combination thereof.

Para. H. The peptide of any one of Paras. A-G, wherein the peptide is cyclized.

Para. I. An isolated fragment of a peptide, wherein the peptide consists of an amino acid sequence of SEQ ID NO:1, and the fragment has a length of 4-16 amino acids.

Para. J. The fragment of Para. I, further comprising N-terminal carboxylation, C-terminal amidation, one or more halogens, or a combination thereof.

Para. K. The fragment of Para. I or Para. J, wherein the fragment is cyclized

Para. L. A pharmaceutical composition comprising a peptide of any one of Paras. A-H or a fragment of any one of Paras. I-K and at least one pharmaceutically acceptable excipient.

Para. M. A method of treating depression in a subject in need thereof, comprising administering to the subject a therapeutically effective amount of a peptide of any one of Paras. A-H or a fragment of any one of Paras. I-K or a composition of Para. L.

Para. N. A method of treating post-traumatic stress disorder (PTSD) in a subject in need thereof, comprising administering to the subject a therapeutically effective amount of a peptide of any one of Paras. A-H or a fragment of any one of Paras. I-K or a composition of Para. L.

Para. O. A method of treating a central nervous system disorder in a subject in need thereof, comprising administering to the subject a therapeutically effective amount of a peptide of any one of Paras. A-H or a fragment of any one of Paras. I-K or a composition of Para. L.

Para. P. The method of Para. O, wherein the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. Q. The method of Para. O, wherein the central nervous system disorder is selected from autism spectrum disorders, bipolar disorder, catalepsy, depression, post-traumatic stress disorder (PTSD), encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. R. A method of treating a neurodevelopmental disorder in a subject in need thereof, comprising administering to the subject a therapeutically effective amount of a peptide of any one of Paras. A-H or a fragment of any one of Paras. I-K or a composition of Para. L.

Para. S. The method of Para. R, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. T. The method of Para. S, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. U. The method of Para. S, wherein the motor disorders are developmental coordination disorder or stereotypic movement disorder.

Para. V. A method of treating Phelan-McDermid Syndrome in a subject in need thereof, comprising administering to the subject a therapeutically effective amount of a peptide of any one of Paras. A-H or a fragment of any one of Paras. I-K or a composition of Para. L.

Para. W. A method of treating depression in a subject in need thereof, comprising administering to the subject a therapeutically effective amount of a peptide having a length of 7 amino acids to 20 amino acids and comprising an amino acid sequence of PKKLRP (SEQ ID NO: 2).

Para. X. A method of treating a central nervous system disorder in a subject in need thereof, comprising administering to the subject a therapeutically effective amount of a peptide having a length of 7 amino acids to 20 amino acids and comprising an amino acid sequence of PKKLRP (SEQ ID NO: 2).

Para. Y. The method of Para. X, wherein the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. Z. A method of treating a neurodevelopmental disorder in a subject in need thereof, comprising administering to the subject a therapeutically effective amount of a peptide having a length of 7 amino acids to 20 amino acids and comprising an amino acid sequence of PKKLRP (SEQ ID NO: 2).

Para. AA. The method of Para. Z, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. AB. The method of Para. AA, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. AC. The method of Para. AA, wherein the motor disorders are developmental coordination disorder or stereotypic movement disorder.

Para. AD. A method of treating Phelan-McDermid Syndrome in a subject in need thereof, comprising administering to the subject a therapeutically effective amount of a peptide having a length of 7 amino acids to 20 amino acids and comprising an amino acid sequence of PKKLRP (SEQ ID NO: 2).

Para. AE. A method of treating depression in a subject in need thereof, comprising administering to the subject a therapeutically effective amount of a peptide consisting of an amino acid sequence of PKKLRP (SEQ ID NO: 2).

Para. AF. A method of treating a central nervous system disorder in a subject in need thereof, comprising administering to the subject a therapeutically effective amount of a peptide consisting of an amino acid sequence of PKKLRP (SEQ ID NO: 2).

Para. AG. The method of Para. AF, wherein the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. AH. A method of treating a neurodevelopmental disorder in a subject in need thereof, comprising administering to the subject a therapeutically effective amount of a peptide consisting of an amino acid sequence of PKKLRP (SEQ ID NO: 2).

Para. AI. The method of Para. AH, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. AJ. The method of Para. AI, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. AK. The method of Para. AI, wherein the motor disorders are developmental coordination disorder or stereotypic movement disorder.

Para. AL. A method of treating Phelan-McDermid Syndrome in a subject in need thereof, comprising administering to the subject a therapeutically effective amount of a peptide consisting of an amino acid sequence of PKKLRP (SEQ ID NO: 2).

Para. AM. A method of treating depression in a subject in need thereof, comprising administering to the subject a therapeutically effective amount of a peptide having a length of 7 amino acids to 20 amino acids and comprising an amino acid sequence having at least 65% sequence identity to SEQ ID NO: 2.

Para. AN. The method of Para. AM, wherein the peptide comprises an amino acid sequence having at least 85% sequence identity to SEQ ID NO: 2.

Para. AO. A method of treating a central nervous system disorder in a subject in need thereof, comprising administering to the subject a therapeutically effective amount of a peptide having a length of 7 amino acids to 20 amino acids and comprising an amino acid sequence having at least 65% sequence identity to SEQ ID NO: 2.

Para. AP. The method of Para. AO, wherein the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. AQ. A method of treating a neurodevelopmental disorder in a subject in need thereof, comprising administering to the subject a therapeutically effective amount of a peptide having a length of 7 amino acids to 20 amino acids and comprising an amino acid sequence having at least 65% sequence identity to SEQ ID NO: 2.

Para. AR. The method of Para. AQ, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. AS. The method of Para. AR, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. AT. The method of Para. AR, wherein the motor disorders are developmental coordination disorder or stereotypic movement disorder.

Para. AU. A method of treating Phelan-McDermid Syndrome in a subject in need thereof, comprising administering to the subject a therapeutically effective amount of a peptide having a length of 7 amino acids to 20 amino acids and comprising an amino acid sequence having at least 65% sequence identity to SEQ ID NO: 2.

Para. AV. The method of any one of Paras. W-AU, wherein the peptide further comprises N-terminal carboxylation, C-terminal amidation, one or more halogens, or a combination thereof.

Para. AW. The method of any one of Paras. W-AV, wherein the peptide is cyclized.

Para. AX. A method of treating depression in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids.

Para. AY. A method of treating a central nervous system disorder in a subject in need thereof, comprising administering to the subject a therapeutically effective amount an isolated fragment of a peptide, wherein the peptide consists of an amino acid sequence of SEQ ID NO: 2, and the fragment has a length of 3-5 amino acids.

Para. AZ. The method of Para. AY, wherein the central nervous system disorder is selected from autism spectrum disorders, bipolar disorder, catalepsy, depression, encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. BA. A method of treating a neurodevelopmental disorder in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids.

Para. BB. The method of Para. BA, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. BC. The method of Para. BB, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. BD. The method of Para. BB, wherein the motor disorders are developmental coordination disorder or stereotypic movement disorder.

Para. BE. A method of treating Phelan-McDermid Syndrome in a subject in need thereof, comprising administering to the subject a therapeutically effective amount of an isolated fragment of a peptide, wherein the peptide consists of an amino acid sequence of SEQ ID NO: 2, and the fragment has a length of 3-5 amino acids.

Para. BF. The method of any one of Paras. AX-BE, wherein the fragment further comprises N-terminal carboxylation, C-terminal amidation, one or more halogens, or a combination thereof.

Para. BG. The method of any one of Paras. AX-BF, wherein the fragment is cyclized.

Para. BH. A isolated peptide having a length of 7 amino acids to 20 amino acids and comprising an amino acid sequence of PKKLRP (SEQ ID NO: 2).

Para. BI. An isolated peptide consisting of an amino acid sequence of PKKLRP (SEQ ID NO: 2).

Para. BJ. An isolated peptide having a length of 7 amino acids to 20 amino acids and comprising an amino acid sequence having at least 65% sequence identity to SEQ ID NO: 2.

Para. BK. The peptide of Para. BJ comprising an amino acid sequence having at least 85% sequence identity to SEQ ID NO: 2.

Para. BL. The peptide of any one of Paras. BH-BK, further comprising N-terminal carboxylation, C-terminal amidation, one or more halogens, or a combination thereof.

Para. BM. The peptide of any one of Paras. BH-BL, wherein the peptide is cyclized.

Para. BN. An isolated fragment of a peptide, wherein the peptide consists of an amino acid sequence of SEQ ID NO: 2, and the fragment has a length of 3-5 amino acids.

Para. BO. The fragment of Para. BN, further comprising N-terminal carboxylation, C-terminal amidation, one or more halogens, or a combination thereof.

Para. BP. The fragment of Para. BN or Para. BO, wherein the peptide is cyclized.

Para. BQ. A pharmaceutical composition comprising a peptide of any one of Paras. BH-BM or a fragment of any one of Paras. BN-BP and at least one pharmaceutically acceptable excipient.

Para. BR. A method of treating depression in a subject in need thereof, comprising administering to the subject a therapeutically effective amount of a peptide of any one of Paras. BH-BM or a fragment of any one of Paras. BN-BP or a composition of Para. BQ.

Para. BS. A method of treating post-traumatic stress disorder (PTSD) in a subject in need thereof, comprising administering to the subject a therapeutically effective amount of a peptide of any one of Paras. BH-BM or a fragment of any one of Paras. BN-BP or a composition of Para. BQ.

Para. BT. A method of treating a central nervous system disorder in a subject in need thereof, comprising administering to the subject a therapeutically effective amount of a peptide of any one of Paras. BH-BM or a fragment of any one of Paras. BN-BP or a composition of Para. BQ.

Para. BU. The method of Para. BT, wherein the central nervous system disorder is selected from autism spectrum disorders, bipolar disorder, catalepsy, depression, post-traumatic stress disorder (PTSD), encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

Para. BV. A method of treating a neurodevelopmental disorder in a subject in need thereof, comprising administering to the subject a therapeutically effective amount of a peptide of any one of Paras. BH-BM or a fragment of any one of Paras. BN-BP or a composition of Para. BQ.

Para. BW. The method of Para. BV, wherein the neurodevelopmental disorder is selected from intellectual disability, autism spectrum disorders, motor disorders, tic disorders, traumatic brain injury, Down syndrome, attention deficit hyperactivity disorder, schizophrenia, schizotypal disorder, hypogonadotropic hypogonadal syndromes, fetal alcohol spectrum disorder, and Minamata disease caused by mercury, or any combination thereof.

Para. BX. The method of Para. BW, wherein the autism spectrum disorders are classical autism or Autistic Disorder; Asperger Syndrome; Childhood Disintegrative Disorder; Pervasive Developmental Disorder—Not Otherwise Specified (PDD-NOS); Fragile X Syndrome; Rett Syndrome; Kanner syndrome; or Phelan-McDermid Syndrome.

Para. BY. The method of Para. BW, wherein the motor disorders are developmental coordination disorder or stereotypic movement disorder.

Para. BZ. A method of treating Phelan-McDermid Syndrome in a subject in need thereof, comprising administering to the subject a therapeutically effective amount of a peptide of any one of Paras. BH-BM or a fragment of any one of Paras. BN-BP or a composition of Para. BQ.

Other embodiments are set forth in the following claims.

What is claimed is:

1. A method of treating a central nervous system disorder in a subject in need thereof, comprising administering to the subject a therapeutically effective amount of an isolated peptide having a length of 7 amino acids to 20 amino acids and comprising the amino acid sequence having at least 65% sequence identity to SEQ ID NO: 2; wherein the central nervous system disorder is selected from autism spectrum disorders, bipolar disorder, catalepsy, depression, post-traumatic stress disorder (PTSD), encephalitis, epilepsy/seizures, locked-in syndrome, meningitis, migraine, multiple sclerosis, myelopathy, neurodegenerative disorders, schizophrenia, obsessive-compulsive disorder, and tic disorders, or any combination thereof.

2. The method of claim 1, wherein the central nervous system disorder is epilepsy/seizures.

3. The method of claim 1, wherein the peptide further comprises N-terminal carboxylation, C-terminal amidation, benzylation, one or more halogens, or a combination thereof.

4. The method of claim 1, wherein the peptide is cyclized.

5. The method of claim 1, wherein the peptide has a length of 7 amino acids to 20 amino acids and comprises the amino acid sequence of PKKLRP (SEQ ID NO: 2).

* * * * *

```
                        SEQUENCE LISTING

<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys His Gly Leu Tyr Asn Leu Lys Gln Cys Lys Met Ser Leu Asn Gly
1               5                   10                  15

Gln

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Lys Lys Leu Arg Pro
1               5
```